United States Patent [19]

Crounse et al.

[11] 3,974,144

[45] Aug. 10, 1976

[54] COMPOUNDS INCLUDING CARBOXYSTYRYLPHENYL GROUP

[75] Inventors: Nathan N. Crounse, Cincinnati, Ohio; Kantilal B. Desai, Highland Heights, Ky.

[73] Assignee: Sterling Drug Inc., New York, N.Y.

[22] Filed: Nov. 19, 1973

[21] Appl. No.: 417,084

Related U.S. Application Data

[63] Continuation-in-part of Ser. No. 224,296, Feb. 7, 1972, Pat. No. 3,833,510.

[30] Foreign Application Priority Data

Jan. 24, 1973 Canada................................ 161971

[52] U.S. Cl............................................ 260/240 CA
[51] Int. Cl.²............... C07D 307/78; C07D 333/52; C07D 405/06; C07D 409/06
[58] Field of Search .............................. 260/240 CA

[56] References Cited
FOREIGN PATENTS OR APPLICATIONS 1,224,664   3/1971   United Kingdom............. 260/240 A

OTHER PUBLICATIONS

Bloom et al. (Defensive Publication) Apr. 1969 Ser. No 778,781 filed Nov. 25, 1968, in 861 O.G. 369.

*Primary Examiner*—Allen B. Curtis
*Attorney, Agent, or Firm*—Lynn T. Fletcher; B. Woodrow Wyatt

[57] ABSTRACT

Benzofurans, benzothiophenes, and naphthofurans which are substituted by carboxystyrylphenyl groups and their corresponding esters and amides are optical brightening agents useful for whitening and brightening natural and synthetic fibers, papers, resins and the like. The compounds are conveniently prepared by interacting benzofurans, benzothiophenes or naphthofurans, which are substituted by a p-tolyl group, with an aromatic aldehyde or preferably the anil derivative thereof.

25 Claims, No Drawings

COMPOUNDS INCLUDING CARBOXYSTYRYLPHENYL GROUP

This application is a contiuation-in-part of prior copending application Ser. No. 224,296, filed Feb. 7, 1972, now U.S. Pat. No. 3,833,510, issued Sept. 3, 1974.

This invention relates to compositions of matter classified in the art of chemistry as substituted benzofurans, benzothiophenes and naphthofurans, to processes for their preparation, and to polymeric compositions containing them.

The compunds of this invention are useful as fluorescent whitening and brightening agents for treatment of threads, sheets, films, filaments, textile fabrics, castings, moldings, and the like as well as in the manufacture of textiles, paper, varnishes, inks, coatings and plastics. These compounds are particularly valuable because of their strong blue shade of fluorescence and their excellent stability to light, chlorine-type bleaches and elevated temperatures.

In its composition of matter aspect, the invention sought to be patented resides in the novel chemical compounds of Formula I

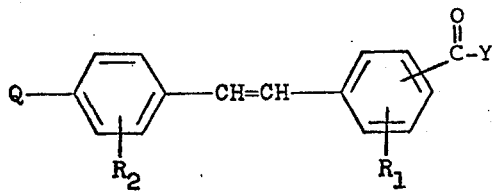

Formula I wherein: Q is a monovalent aromatic heterocyclic radical selected from the class having the formulas

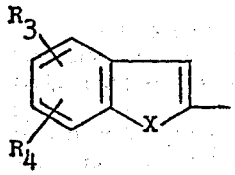 and

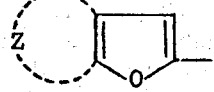

X is oxygen or surfur; Y is —OR or

in which R is hydrogen, lower alkyl having one to six carbon atoms, hydroxy-lower alkyl having two or three carbon atoms, phenyl, benzyl, phenethyl or phenyl, benzyl or phenethyl substituted in the benzene ring thereof by lower alkyl of one to six carbon atoms, halo or alkoxy of one to six carbon atoms; $R^o$ is hydrogen, lower alkyl having one to three carbon atoms, phenyl, benzyl, phenethyl or phenyl, benzyl or phenethyl substituted in the benzene ring thereof by lower alkyl of one to six carbon atoms, halo or alkoxy of one to six carbon atoms; $Y^o$ is hydrogen or lower alkyl having one to three carbon atoms; $R^o$ and $Y^o$ taken together with the nitrogen atom to which they are commonly bonded are pyrrolidino, piperidino or morpholino; $R_1$ and $R_2$ are the same or different and are members of the class consisting of hydrogen, alkyl having one to six carbon atoms, alkoxy having one to six carbon atoms, and halo; $R_3$ and $R_4$ are the same or different and are members of the class cosisting of hydrogen, alkyl having one to six carbon atoms, alkoxy having one to six carbon atoms, cyano, halo, dialkylamino wherein each alkyl has one to six carbon atoms, alkanoylamino having one to six carbon atoms, phenyl, phenyl substituted by alkyl having one to six carbon atoms, halo, alkoxy having one to six carbon atoms, and alkanoylamino having one to six carbon atom; and Z is naphtho.

In the first of its process aspects, the invention sought to be patented resides in the method which comprises interacting a compound of the formula

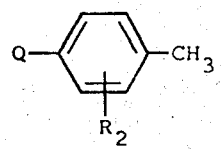

Formula II with an aldehyde of the formula

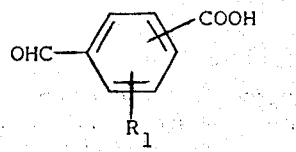

or the anil thereof to produce a compound of Formula I in which Y is —OR wherein R is hydrogen, and Q, $R_1$, $R_2$, $R_3$, $R_4$, X and Z each have the same significance as in Formula I, to yield a stilbene compound of Formula I in which Y is —OH.

In a second process aspect, the invention sought to be patented resides in the method for preparing a compound of Formula I in which Y is —OR wherein R has the same meanings given in Formula I except hydrogen, which comprises esterifying a compound of the formula

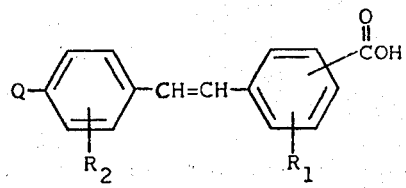

by interacting the compund or an appropriate carboxylic functional derivative thereof wherein Q is a monovalent aromatic heterocyclic radical selected from the class having the formulas

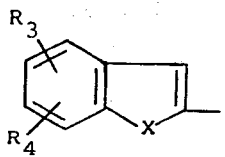 and

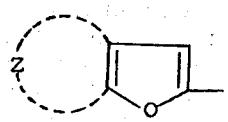 ; and $R_1$, $R_2$, $R_3$, $R_4$, X and Z each have the same meanings given in Formula I, with the appropriate compound of the formula R—OH in which R has the same meanings given in Formula I except hydrogen.

In a third process aspect, the invention sought to be patented resides in the method for preparing a compound of Formula I in which Y is $$-N\begin{matrix}R^o\\Y^o\end{matrix}$$

wherein $R^o$ and $Y^o$ each have the same meanings given in Formula I which comprises amidating a compund of the formula

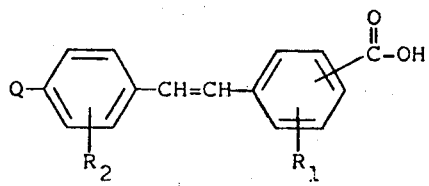

by interacting the compound or appropriate carboxylic functional derivative thereof wherein Q is a monovalent aromatic heterocyclic radical selected from the class having the formulas

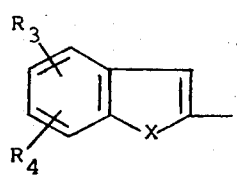 and

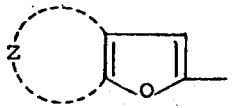 ; and $R_1$, $R_2$, $R_3$, $R_4$, X and Z each have the same meanings given in Formula I, with the appropriate compound of the formula $$HN\begin{matrix}R^o\\Y^o\end{matrix}$$

in which $R^o$ and $Y^o$ each have the same meanings given in Formula I.

In a fourth process aspect, the invention sought to be patented resides in the method for preparing a compound of Formula I in which Y is —OR wherein R is lower alkyl having one to six carbon atoms, hydroxy-lower alkyl having two or three carbon atoms, benzyl, phenethyl or benzyl or phenethyl substituted in the benzene ring thereof by lower alkyl of one to six carbon atoms, halo or alkoxy of one to six carbon atoms which comprises interacting a compound of the formula

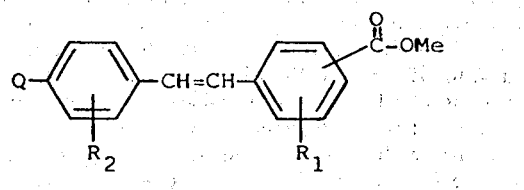

wherein Me is an alkali metal; Q is a monovalent aromatic heterocyclic radical selected from the class having the formulas

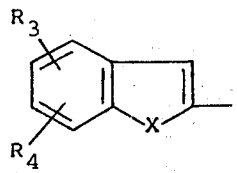 and

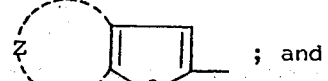 ; and $R_1$, $R_2$, $R_3$, $R_4$, X and Z each have the same meanings given in Formula I, with an appropriate compound represented by R-halogen in which R is lower alkyl having one to six carbon atoms, hydroxy-lower alkyl having two or three carbon atoms, benzyl, phenethyl or benzyl or phenethyl substituted in the benzene ring thereof by lower alkyl of one to six carbon atoms, halo or alkoxy of one to six carbon atoms.

When R in the formulas herein is hydroxy-lower alkyl having two or three carbon atoms, there are included —$CH_2CH_2OH$, —$CH(OH)CH_3$, —$CH_2CH_2CH_2OH$, —$CH_2CH(OH)CH_3$ and —$CH(OH)CH_2CH_3$.

As used in defining R, $R_1$, $R_2$, $R_3$ and $R_4$ in the formulas and elsewhere herein, the term "lower alkyl having one to six carbon atoms" includes, for example, methyl, ethyl, propyl, isoproyl, butyl, sec-butyl, tert-butyl, isobutyl, amyl, hexyl, 2,3-dimethylbutyl, and the like.

As used in defining $R_1$, $R_2$, $R_3$ and $R_4$ in the formulas and elsewhere herein, the term "alkoxy having one to six carbon atoms" includes, for example, methoxy, ethoxy, propoxy, isopropoxy, butoxy, isobutoxy, tert-butoxy, amyloxy, hexyloxy, and the like.

As used in defining $R_1$, $R_2$, $R_3$ and $R_4$ in the formulas and elsewhere herein, the term "halo" includes chloro, fluoro, bromo and iodo. The preferred halo substituent is chloro because the other halogens offer no particular advantages over chloro and because of the relatively low cost and ease of preparation of the required chloro intermediates. However, the other above-named halo substituents are also satisfactory.

As used in defining $R^0$ in the formulas and elsewhere herein, the term "lower alkyl having one to three carbon atoms" includes methyl, ethyl, propyl and isopropyl.

When $R_3$ and $R_4$ in the formulas herein are dialkylamino, each alkyl group having from one to six carbon atoms, there are included for example, dimethylamino, diethylamino, dipropylamino, dibutylamino, dipentylamino, dihexylamino, methylethylamino, N-methyl-N-butylamino, and the like. For the purposes of this invention the common amino radicals wherein the two alkyl groups are joined to form a ring, for example, pyrrolidino, piperidino, morpholino, thiomorpholino, and N-methylpiperazino, are equivalent to the dialkylamino compounds claimed herein.

When $R_3$ and $R_4$ in the formulas herein are alkanoylamino having one to six carbon atoms, there are included, for example, formamido, acetamido, propionamido, butyramido, isobutyramido, valeramide, isovaleramido, caproamido, and the like.

When $R_3$, and $R_4$ in the formulas herein are substituted phenyl, there are included, for example, p-tolyl, o-tolyl, m-tolyl, p-ethylphenyl, p-acetamidophenyl, o-acetamidophenyl, m-hexanoylaminophenyl, p-chlorophenyl, o-chlorophenyl, m-bromophenyl, o-methoxyphenyl, p-ethoxyphenyl, 2,4-dimethoxyphenyl, 3,4-dichlorophenyl, 2,4-dimethylphenyl, and the like.

In general, the compounds of Formula I are highmelting yellow solids. They are insoluble in water, the lower alcohols, ketones and mineral acids and moderately soluble in dimethylformamide and high-boiling, nonpolar aromatic hydrocarbons. The alkali metal or ammonium salts of the carboxylic acid substituted compounds have low solubility in water and are generally sparingly soluble in 2-ethoxyethanol and dimethylformamide.

When the compounds of the present invention are dispersed or dissolved in aqueous media, they fluoresce blue-water under ultraviolet light. They are particularly substantive to a wide variety of natural and synthetic fibers, for example cotton, cellulose acetate, viscose rayon and nylon, and are absorbed by such fibers from very low concentrations in aqueous dispersions. Furthermore the compounds of this invention are particularly adapted to incorporation into plastic and synthetic fiber melts and to application to fibrics by the known heat-setting procedures. These compounds also have high stability to sunlight, soap, synthetic detergents and chlorine-type bleaches.

The above-described properties of the compounds of Formula I make them especially valuable as fluorescent whitening and brightening agents in treating white and colored fabrics in order to neutralize the yellowness which develops with age in white textiles and to enhance the billiance of colored textiles. In such utilization the high resistance of these compounds to chlorine bleaches and to light are distinct advantages. Another valuable advantage offered by these compounds is their unusual stability at high temperatures, which permits their use in high melting polymers. A further important advantage of the compounds of this invention lies in their property of building up the amount of the whitening agent without developing an undesirable discoloration, for example a reddish or gray color, such as is produced by many of the known optical bleaching agents when they are applied repeatedly, as in successive launderings.

The manner and process of making and using the invention, and the best mode contemplated by the inventor of carrying out the invention, will now be described so as to enable any person skilled in the art to which it pertains to make and use the same.

In general, the compounds of this invention wherein R in Formula I is hydrogen are conveniently obtained by interacting an appropriate carboxylic acid-substituted benzaldehyde (for example, a phthalaldehydic acid, an isophthalaldehyde acid or a terephthalaldehydic acid) or preferably the anil derivative of such aromatic carboxaldehyde, with a compound having the structure

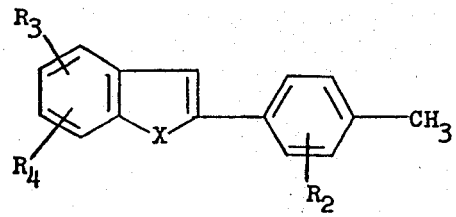

Formula III for obtaining those final products in which Q is a benzofuran or benzothiophene moiety and with a compound having the structure

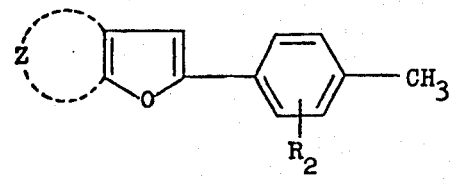

Formula IV for obtaining those final products in which Q is a naphthofuran moiety. The symbols $R_2$, $R_3$, $R_4$, X and Z each have the same respective meanings as herebefore given with respect to Formula I. This reaction can usually be carried out at moderate temperatures, for instance in the range 0–90°C, in a suitable solvent and in the presence of a strongly alkaline reagert. Under these conditions, the reaction is generally complete in approximately one-half to 3 hours.

Suitable solvents are those highly polar solvents which are free of acidic hydrogen or other atoms or radicals which may react with strongly alkaline reagents. Examples of suitable solvents include dimethylformamide, dimethylacetamide, diethylformamide, hexamethylphosphoramide, N-formylpiperidine, and sulfolane.

The strongly alkaline reagents suitable for the condensation include the alkali metal salts of tertiary aliphatic alcohols, alkali metal hydroxides, alkali metal amides and alkali metal hydrides. However, the nature of the alkaline reagent (other than its basicity) is not critical to the invention, and any alkaline compound of comparable basicity under the reaction conditions can be employed herein.

Because of the reactive nature of the alkaline reagent, it is preferable to conduct this condensation reaction in a manner which will exclude atmospheric moisture and carbon dioxide. Accordingly, for such purpose an atmosphere of dry nitrogen or other inert gas over the reaction medium is provided.

The compounds of Formula I in which Y is —OR wherein R is other than hydrogen, that is, lower alkyl, hydroxy-lower alkyl, phenyl, benzyl or phenethyl esters of our invention, are readily prepared by esterifying a free carboxylic acid compound of Formula I with the appropriate lower alkanol, lower alkanediol, phenol, benzyl alcohol or phenethyl alcohol, respectively. The esterification of the free carboxylic acid substituted compounds of Formula I (wherein R in —OR is hydrogen) to obtain the corresponding compounds of the same formula in which R is lower alkyl, hydroxy-lower alkyl, phenyl, benzyl or phenethyl is accomplished by utilizing any one of several art-known methods for preparing carboxylic esters from appropriate carboxylic functional derivatives, for example, free carboxylic acids, carboxylic acid halides or other esters. However, it is particularly convenient for the purposes of this invention to utilize the free carboxylic acid compounds of Formula I in the well-known two-step method which comprises first converting the carboxylic acid to the corresponding acid chloride and then interacting the acid chloride with the desired lower alkanol, lower alkanediol, phenol, benzyl alcohol or phenethyl alcohol.

Alternatively, the compounds of Formula I in which Y is -OR wherein R is an aliphatic or arylaliphatic moiety, can be conveniently prepared by interacting an alkali metal salt of an appropriate carboxylic acid compound of Formula I with the appropriate aliphatic or arylaliphatic halide.

The compounds of Formula I in which Y is

that is, the amide final products of our invention, are readily prepared by amidating a free carboxylic acid compound of Formula I, or an appropriate carboxylic functional derivative thereof with the appropriate primary or secondary amine. The amidation of the free carboxylic acid substituted compounds of Formula I (wherein Y is —OR in which R is hydrogen) to obtain the corresponding compounds of the same formula in which $R^0$ is hydrogen, a lower alkyl, hydroxy-lower alkyl, phenyl, benzyl or phenethyl moiety and $Y^0$ is hydrogen or a lower alkyl moiety is accomplished by employing any one of several art-known methods for preparing carboxylic amides from appropriate carboxylic functional derivatives, for example, free carboxylic acids, carboxylic acid halides or carboxylic esters. However, it is particularly convenient for the purposes of our invention to utilize the free carboxylic acid compounds of Formula I by first converting the carboxylic acid to the corresponding acid chloride and then interacting the acid chloride with the desired primary or secondary amine.

The requisite 2-(p-tolyl)-substituted intermediates of Formulas III and IV are generally known compounds prepared according to procedures well known to those skilled in the art, for instance by cyclizing an appropriate phenyl or naphthyl 4-methylphenacyl ether or thioether.

The carboxylic acid-substituted products which represent one group of final products of this invention and which are also intermediates to the corresponding ester and amide final products, can be obtained by the interaction of the p-tolyl-substituted compounds of Formula III and Formula IV, with the appropriate carboxylic acid-substituted benzaldehyde. However, it is preferred to use the anil derivative of the aromatic carboxaldehyde because of the substantially higher degree of reactivity of these derivatives than that of the aldehyde with the p-tolyl-substituted starting materials. The requisite anil derivatives and methods for their preparation, for example, by the interaction of aniline with the aromatic carboxaldehyde, are well known and have been described in the prior art. Although the anil derivatives employed in this invention were prepared from unsubstituted aniline, it will be obvious that anilines bearing substituents on the ring, which are inert under the conditions of the processes of this invention, for example, lower alkyl, lower alkoxy, halogen, etc. can also be employed, if desired.

The derivatives obtained by the reaction of aniline with each of the three carboxylic acid-substituted benzaldehydes, that is, phthalaldehydic acid, isophthalaldehydic acid, and terephthalaldehydic acid, have been described in the literature. The aniline derivatives of isophthalaldehydic acid and of terephthalaldehydic acid are described as existing in the imine (Schiff's base) form (anils). On the other hand, the aniline derivative of phthalaldehydic acid is described as being the cyclic compound, 3-anilinophthalide. This intermediate is as fully reactive and useful in the processes of this invention for obtaining the 2-carboxystyryl-substituted compound as are the anils of the isophthalaldehydic and terephthalaldehydic acids for obtaining the 3-carboxystyryl- and the 4-carboxystyryl-substituted compounds, respectively. Accordingly, as used throughout this application, the term "anil" is intended to include the cyclic 3-anilinophthalides obtained from the phthalaldehydic acids as well as the imine forms obtained from the isophthalaldehydic and the terephthalaldehydic acids.

A preferred mode of utilizing the compounds of Formula I is to incorporate them into melts of synthetic plastic material for spinning synthetic fibers or for casting or molding plastics in an appropriate concentration, for example 0.01 to 0.1 percent by weight of the melt.

A further method of utilizing the compounds of Formula I is to impregnate textile fabrics comprising synthetic fibers, for example polyester (poly[terephthalic acid ethylene glycol ester]) or nylon, with an aqueous dispersion of the compound at temperatures below about 75°C, for example, at room temperature and then to subject the treated fabric to a dry heat treatment at a temperature above 100°C. The fabric may advantageously be dried at temperatures in the range 60°–100°C prior to the heat treatment, which is preferably carried out at temperatures in the range 125°–250°C. Said heat treatment may be accomplished by any of several known methods, for example, by heating in a drying chamber, by ironing the fabric, or by treating it with dry superheated steam.

The structures of the compounds of this invention were established by the modes of synthesis, by elementary analysis, and by ultraviolet, infrared and nuclear magnetic resonance spectra. The course of the reactions was followed and the homogeneity of the products thus obtained was ascertained by use of thin layer chromatography.

The invention is illustrated by the following examples without, however, being limited thereto. Melting points are uncorrected except where otherwise indicated.

EXAMPLE 1

A stirred solution of 2.24 g (0.01 mole) of 2-(p-tolyl)benzothiophene and 2.25 g (0.01 mole) of the anil derivative of terephthalaldehydic acid in 150 ml of freshly distilled, dry dimethylformamide was flushed with nitrogen for 10 minutes. The solution was heated to 35°C and 6.72 g (0.06 mole) of potassium tert-butoxide was added. The color of the reaction mixture changed from violet to brown. Analysis of an aliquot by ultraviolet spectroscopy showed that the reaction was completed after 2 hours of stirring. Glacial acetic acid was added in amount sufficient to neutralize excess potassium tert-butoxide, and the reaction mixture was heated to reflux and filtered while hot to collect the resulting precipitate. The filter cake was washed with hot dimethylformamide containing two percent aniline, then slurried in hot ten percent aqueous hydrochloric acid and refiltered. The collected precipitate was washed on the filter with water until free of acid and then dried in vacuo. The product was finally purified by sublimation to obtain 2-[4-(4-carboxystyryl)phenyl]-benzothiophene which remained unmelted at 350°C. The wavelength of maximum excitation of this compound was 367 nm and the wavelength of maximum emission was 423 nm.

EXAMPLE 2

Proceeding in a manner similar to that described in Example 1 above, 2-(p-tolyl)benzofuran (2.08 g; 0.01 mole) was interacted with 2.25 g (0.01 mole) of the anil derivative of terephthalaldehydic acid in the presence of 6.72 g (0.06 mole) of potassium tert-butoxide in 150 ml of dimethylformamide. The resulting product was purified by sublimation to obtain 2-[4-(4-carboxystyryl)phenyl]benzofuran which melted at 348°–349°C. The wavelength of maximum excitation of this compound was 365 nm and the wavelength of maximum emission was 425 nm.

EXAMPLE 3

Following the procedure outlined in Example 1 above, 5-phenyl-2-(p-tolyl)benzofuran was interacted with an equimolar quantity of the anil derivative of terephthalaldehydic acid to give 5-phenyl-2-[4-(4-carboxystyryl)-phenyl]benzofuran. After purification by sublimation, the product remained unmelted at 350°C. The wavelength of maximum excitation of this compound was 371 nm and the wavelength of maximum emission was 432 nm.

EXAMPLE 4

Proceeding in a manner similar to that in Example 1 above, 5-methoxy-2-(p-tolyl)benzofuran was reacted with an equimolar quantity of the anil derivative of terephthalaldehydic acid to produce 5-methoxy-2-[4-(4-carboxystyryl)phenyl]benzofuran, which when purified by sublimation, remained unmelted at 350°C. The wavelength of maximum excitation of this compound was 376 nm, and the wavelength of maximum emission was 440 nm.

EXAMPLE 5

When 5-chloro-2-(p-tolyl)benzofuran was condensed with the anil derivative of terephthalaldehydic acid according to the procedure described in Example 1, there was obtained 5-chloro-2-[4-(4-carboxystyryl)-phenyl]benzofuran which melted at 347°–348°C following recrystallization from trichlorobenzene. The wavelength of maximum excitation of this compound was 372 nm and the wavelength of maximum emission was 424 nm.

EXAMPLE 6

7½ Grams (0.02 mole) of 5-chloro-2-[4-(4-carboxystyryl)phenyl]benzofuran prepared in accordance with the procedure described in Example 5 above, was reacted with thionyl chloride in 400 ml of chlorobenzene at 70°C. The excess thionyl chloride and chlorobenzene were distilled off. To the acid chloride remaining in the flask, there was added 200 g (6.25 mole) of methyl alcohol in the presence of 4.0 ml of pyridine. The reaction mixture was refluxed for sixteen hours, and then allowed to cool. The resulting product was collected on a filter and was purified by recrystallization from dichlorobenzene and cyclohexanone. The 5-chloro-2-[4-(4-carbomethoxystyryl)phenyl]benzofuran thus obtained melted at 265°–267°C. The wavelength of maximum excitation of this compound was 372 nm and the wavelength of maximum emission was 436 nm.

EXAMPLE 7

Proceeding in a manner similar to that in Example 6 above, 5-chloro-2-[4-(4-carboxystyryl)phenyl]benzofuran was interacted with thionyl chloride and the acid chloride was then interacted with ethylene glycol in the presence of pyridine. The product, when recrystallized from dichlorobenzene, gave pure 5-chloro-2-{4-[4-carbo(2-hydroxyethoxy)styryl]phenyl}benzofuran which melted at 239°– 243°C. This compound showed maximum excitation wavelength at 373 nm and showed maximum emission wavelength at 439 nm.

EXAMPLE 8

Following the procedure outlined in Example 5 above, except that 3-anilinophthalide was used in place of the anil derivative of terephthalaldehydic acid, there was obtained 5-chloro-2-[4-(2-carboxystyryl)phenyl]-benzofuran. The product was subjected to purification by reprecipitation of the free acid with hydrogen chloride gas from a solution of the sodium salt in ethanol. The dried, reprecipitated product melted at 290°–295°C, and showed the wavelength of maximum excitation at 362 nm and the wavelength of maximum emission at 417 nm.

EXAMPLE 9

Following the procedure outlined in Example 8 above, 2-(p-tolyl)naphtho[2,1-b]furan was interacted with an equimolar amount of 3-anilinophthalide. After recrystallization from chlorobenzene, the thus obtained 2-[4-(2-carboxystyryl)phenyl]naphtho[2,1-b]furan melted at 233°–235°C. The wavelength of maximum excitation of this compound was 377 nm and the wavelength of maximum emission was 448 nm.

EXAMPLE 10

Following the procedure as in Example 8, 2-(p-tolyl)-naphtho[1,2-b]furan was interacted with an equimolar quantity of 3-anilinophthalide to produce 2-[4-(2-carboxystyryl)phenyl]naphtho[1,2-b]furan which, when crystallized from chlorobenzene, melted at 210°–211°C. The measured wavelength of maximum excitation was 374 nm and wavelength of maximum emission was 438 nm.

EXAMPLE 11 a. A stirred mixture of 40.75 g (0.25 mole) of 3,4-dichlorophenol, 42.12 g (0.25 mole) of p-methylphenacyl chloride, 38.0 g (0.275 mole) of potassium carbonate, 1.87 g of potassium iodide and 500 ml of acetone was refluxed with stirring for 8 hours. The reaction mixture was allowed to cool and then poured into a large excess of cold water. A solid separated which was collected and washed free of alkali with water. Following recrystallization from 2-ethoxyethanol, the thus obtained ω-(3,4-dichlorophenoxy)-p-methylacetophenone melted at 118°–119°C.

b. In a flask, 250 ml of polyphosphoric acid was stirred and heated to 180°C and to it there was added 36.9 g (0.125 mole) of ω-(3,4-dichlorophenoxy)-p-methylacetophenone from (a) above. The reaction mixture was stirred and held at a temperature between 180°–190°C for 8 hours. The progress of the reaction was followed by ultraviolet spectroscopy and the completion of the reaction was shown by the disappearance of the curve characteristics of the starting material and the appearance of a new maximum at 313 nm. The reaction mixture was allowed to cool and was poured into water. The solid that separated was collected on a filter, washed free of acid and recrystallized from 2-ethoxyethanol to obtain 5,6-dichloro-2-(p-tolyl)benzofuran, melting at 129°–130°C.

c. Following the procedure described in Example 1 above, equimolar quantities of the above-named 5,6-dichloro-2-(p-tolyl)benzofuran and anil derivative of terephthalaldehydic acid were interacted in the presence of potassium tert-butoxide to give 5,6-dichloro-2-[4-(4-carboxystyryl)-phenyl]benzofuran, which, following sublimation, melted at 318,°–322°C. The wavelength of maximum excitation of this compound was 367 nm, and the wavelength of maximum emission was 421 nm.

EXAMPLE 12 a. Following the procedure outlined in Example 11(a), 4-fluorophenol was interacted with an equimolar quantity of p-methylphenacyl chloride in the presence of potassium carbonate to give ω-(4-fluorophenoxy)-p-methylacetophenone which melted at 95°–96°C after recrystallization from methanol.

b. Following the procedure given in Example 11(b), the above-named ω-(4-fluorophenoxy)-p-methylacetophenone was heated with polyphosphoric acid to give 5-fluoro-2-(p-tolyl)benzofuran which, following recrystallization from 2-ethoxyethanol, melted at 156°–157°C. This compound showed the wavelength of maximum excitation at 313 nm and the wavelength of maximum emission at 348 nm.

c. The 5-fluoro-2-(p-tolyl)benzofuran from (b) above was condensed with an equimolar quantity of the anil derivative of terephthalaldehydic acid according to the method described in Example 1 above, to obtain 5-fluoro-2-[4-(4-carboxystyryl)phenyl]benzofuran. When purified by sublimation this product remained unmelted at 350°C. The wavelength of maximum excitation of this compound was 373 nm and the wavelength of maximum emission was 422 nm.

EXAMPLE 13

Proceeding in a manner similar to that used in Example 1, 5-methyl-2-(p-tolyl)benzofuran (2.22 g; 0.01 mole) was interacted with 2.25 g (0.01 mole) of the anil derivative of terephthalaldehydic acid in the presence of 6.72 g (0.06 mole) of potassium tert-butoxide in 150 ml of dimethylformamide. The product thus produced was sublimed to obtain 5-methyl-2-[4-(4-carboxystyryl)phenyl]benzofuran, melting at 355°–358°C. The wavelength of maximum excitation of this compound was 374 nm and the wavelength of maximum emission was 437 nm.

EXAMPLE 14 a. A mixture of 24.2 g (0.1 mole) of 5-chloro-2-(p-tolyl)benzofuran and 32.20 g (0.36 mole) of cuprous cyanide in 100 ml. of 1-methyl-2-pyrrolidone was refluxed for 26 hours. The reaction mixture was allowed to cool to 75°C and the separated solid was collected by filtration. The product was washed with concentrated ammonia to remove the excess cuprous cyanide and the last traces of cuprous cyanide were removed by dissolving the ammonic washed compound in hot chlorobenzene and filtering. On cooling, 5-cyano-2-(p-tolyl)benzofuran separated from the chlorobenzene solution. After collection and drying in vacuo, the product melted at 190°–191°C.

b. Following the procedure given in Example 1, 5-cyano-2-(p-tolyl)benzofuran from above was reacted with an equimolar quantity of the anil derivative of terephthalaldehydic acid in the presence of potassium tert-butoxide using dimethylformamide as a solvent. Upon purification by sublimation, the thus obtained 5-cyano-2-[4-(4-carboxystyryl)phenyl]benzofuran melted at 331°–333°C. The compound had the wavelength of maximum excitation at 366 nm and the wavelength of maximum emission at 423 nm.

EXAMPLE 15

When an equivalent amount of 5-methoxy-3-anilinophthalide is substituted for the anil derivative of terephthalaldehydic acid in the procedure described in Example 1 above, there is obtained as the product 2-[4-(2-carboxy-5-methoxystyryl)phenyl]benzothiophene.

EXAMPLE 16

When an equivalent amount of the anil derivative of 4-methyl-6-methoxyisophthalaldehydic acid is substituted for the anil derivative of terephthalaldehydic acid in the procedure described in Example 2 above, there is obtained as the product 2-[4-(6-methyl-4-methoxy-3-carboxystyryl)phenyl]benzofuran.

EXAMPLE 17

Following the procedure described in Example 3 above but using an equivalent amount of 6-bromo-3-anilinophthalide in place of the anil derivative of terephthalaldehydic acid, there is obtained as the product 5-phenyl-2-[4-(2-carboxy-4-bromostyryl)phenyl]benzofuran.

EXAMPLE 18

When an equivalent amount of 6-methoxy-7-ethoxy-3-anilinophthalide is substituted for the anil derivative of terephthalaldehydic acid in the procedure described in Example 12(c) above, there is obtained as the product 5-fluoro-2-[4-(2-carboxy-3-ethoxy-4-methoxystyryl)phenyl]benzofuran.

EXAMPLE 19

When an equivalent amount of the anil derivative of 5-chloro-3-anilinophthalide is substituted for the anil derivative of terephthalaldehydic acid in the procedure described in Example 4 above, there is obtained as the product 5-methoxy-2-[4-(2-carboxy-5-chlorostyryl)-phenyl]benzofuran.

EXAMPLE 20

Following the procedure described in Example 5 above but using an equivalent amount of the anil derivative of 3-methylterephthalaldehydic acid in place of the anil derivative of terephthalaldehydic acid, there is obtained as the product 5-chloro-2-[4-(2-methyl-4-carboxystyryl)phenyl]benzofuran.

EXAMPLE 21

When an equivalent amount of 5,7-dimethoxy-3-anilinophthalide is substituted for the anil derivative of terephthalaldehydic acid in the procedure described in Example 13 above, there is obtained as the product 5-methyl-2-[4-(2-carboxy-3,5-dimethoxystyryl)-phenyl]benzofuran.

EXAMPLE 22

Following the procedure described in Example 9 above but using an equivalent amount of the anil derivative of 3-bromoterephthalaldehydic acid in place of 3-anilinophthalide, there is obtained as the product 2-[4-(2-bromo-4-carboxystyryl)phenyl]naphtho[2,1-b]furan.

EXAMPLE 23

Similarly, when an equivalent amount of the anil derivative of 3-bromoterephthalaldehydic acid is substituted for the 3-anilinophthalide in the procedure described in Example 10 above, there is obtained as the product 2-[4-(2-bromo-4-carboxystyryl)phenyl]naphtho[1,2-b]furan.

EXAMPLE 24

When an equivalent amount of 7-methyl-3-anilinophthalide is substituted for the anil derivative of terephthalaldehydic acid in the procedure described in Example 11(c) above, there is obtained as the product 5,6-dichloro-2-[4-(2-carboxy-3-methylstyryl)phenyl]benzofuran.

EXAMPLE 25

Following the procedure described in Example 14(b) above but using an equivalent amount of 5,7-dimethoxy-3-anilinophthalide in place of the anil derivative of terephthalaldehydic acid, there is obtained as the product 5-cyano-2-[4-(2-carboxy-3,5-dimethoxystyryl)phenyl]benzofuran.

EXAMPLE 26

Following the procedure outlined in Example 5 above, except tht the anil derivative of isophthalaldehydic acid was used in place of the anil derivative of terephthalaldehydic acid, there was obtained 5-chloro-2-[4-(3-carboxystyryl)phenyl]benzofuran. The product was subjected to purification by recrystallization from boiling o-dichlorobenzene with the aid of decolorizing charcoal. The dried, recrystallized product melted at 309°–312°C, and showed the wavelength of maximum excitation at 352 nm and the wavelength of maximum emission at 409 nm.

EXAMPLE 27

A reaction mixture of 2.08 g (0.01 mole) of 2-(p-tolyl)benzofuran and 2.86 g (0.011 mole) of the p-chloro anil derivative of terephthalaldehydic acid in 25 ml of freshly distilled, dry dimethylformamide was flushed with nitrogen for five minutes. The reaction mixture was heated to 50°C and 4.80 g (0.05 mole) of sodium tert-butoxide in 25 ml of dry dimethylformamide was added. The reaction was carried out first at 50°C. for 2 hours and then at 90°C for 3 hours. At this stage, analysis of an aliquot by ultraviolet spectroscopy showed that the formation of the sodium salt of 5-chloro-2[4-(4-carboxystyryl)phenyl]benzofuran was essentially complete. To the reaction mixture there was added 6.325 g (0.05 mole) of benzyl chloride. The reaction mixture was then heated at reflux during four hours and then allowed to cool. The resulting product was collected on a filter and was purified by recrystallization from dimethylformamide. The 5-chloro-2-[ 4-carbobenzyloxystyryl)phenyl]benzofuran thus obtained melted at 241°–244°C. The wavelength of maximum excitation of this compound was 367 nm and the wavelength of maximum emission was 442 nm.

EXAMPLE 28

Proceeding in a manner similar to that in Example 27 above, except that dimethyl sulfate was used in place of the benzyl chloride, there was obtained 5-chloro-2-[4-(4-carbomethoxystyryl)phenyl]benzofuran melting at 264°–266°C. The wavelength of maximum excitation of this compound was 366 nm and the wavelength of maximum emission was 438 nm.

EXAMPLE 29

A mixture of 8.25 g (0.02 mole) of the potassium salt of 5-chloro-2-[4-(4-carboxystyryl)phenyl]benzofuran and 82.5 ml of chlorobenzene was stirred and treated with 2.2 ml (0.03 mole) of thionyl chloride. The mixture was heated at reflux for 2½ hours and the excess thionyl chloride was removed by distillation. To the cooled residue there was then added 1.71 g (0.021 mole) of anhydrous dimethylamine hydrochloride, 3.5 ml (0.044 mole) of dry pyridine and 35 ml of chlorobenzene. The resulting mixture was stirred and refluxed for 8 hours. After cooling, the reaction mixture was filtered and the solid collected on the filter funnel was washed with chlorobenzene and then methanol. The washed solid was then stirred with water, refiltered, washed free of salt and finally dried. The product was recrystallized from o-dichlorobenzene to yield 5-chloro-2-[4-(4-N,N-dimethylcarbamoylstyryl)phenyl]-benzofuran melting at 290°–294°C. The wavelength of maximum excitation of this compound was 361 nm and the wavelength of maximum emission was 418 nm.

EXAMPLE 30

Following the procedure described in Example 29 above but using benzylamine in place of dimethylamine hydrochloride, there is obtained as the product 5-chloro-2-[4-(4-N-benzylcarbamoylstyryl)phenyl]benzofuran.

EXAMPLE 31

Similarly, when aniline is substituted for the dimethylamine hydrochloride in the procedure described in Example 29 above, there is obtained as the product 5-chloro-2-[4-(4-N-phenylcarbamoylstyryl)phenyl]benzofuran.

EXAMPLE 32

When ammonia is substituted for the dimethylamine hydrochloride in the procedure described in Example 29 above, there is obtained as the product 5-chloro-2-[4-(4-carbamoylstyryl)phenyl]benzofuran.

EXAMPLE 33

Similarly, when isopropylamine is substituted for the dimethylamine hydrochloride in the procedure described in Example 29 above, there is obtained as the product 5-chloro-2[4-(4-N-isopropylcarbamoylstyryl)phenyl]benzofuran.

EXAMPLE 34

Similarly, when N-methylethylamine is substituted for the dimethylamine hydrochloride and the potassium salt of 5-phenyl-2-[4-(4-carboxystyryl)phenyl]benzothiophene for the potassium salt of 5-chloro-2-[4-(4-carboxystyryl)phenyl]benzofuran in the procedure described in Example 29 above, there is obtained as the product 5-phenyl-2-[4-(4-N-ethyl-N-methylcarbamoylstyryl)phenyl]benzothiophene.

EXAMPLE 35

Following the procedure outlined in Example 29 above but using phenethylamine in place of dimethylamine hydrochloride and the potassium salt of 5-methyl-2-[4-(2-carboxystyryl)phenyl]benzofuran instead of the potassium salt of 5-chloro-2-[4-(4-carboxystyryl)phenyl]benzofuran, there is obtained as the product 5-methyl-2-[4-(2-N-phenethylcarbamoylstyryl)phenyl]benzofuran.

EXAMPLE 36

When N-methylbenzylamine is substituted for the dimethylamine hydrochloride and the potassium salt of 5-methoxy-2-[4-(3-carboxystyryl)phenyl]benzofuran instead of the potassium salt of 5-chloro-2[4-(4-carboxystyryl)phenyl]benzofuran in the procedure described in Example 29 above, there is obtained as the product 5-methoxy-2-[4-(3-N-methyl-N-benzylcarbamoylstyryl)phenyl]benzofuran.

EXAMPLE 37

Following the procedure described in Example 27 above but using α-chloro-p-xylene in place of benzyl chloride and the sodium salt of 5-cyano-2-[4-(3-carboxystyryl)phenyl]benzothiophene instead of the sodium slt of 5-chloro-2-[4-(4-carboxystyrylphenyl]benzofuran, there is obtained as the product 5-cyano-2-[4-(3-carbo-p-methylbenzyloxystyryl)phenyl]benzothiophene.

EXAMPLE 38

Similarly, when 2-bromoethylbenzene is substituted for the benzyl chloride and the sodium salt of 2-[4-(4-carboxystyryl)phenyl]naphtho[1,2-b]furan for the sodium salt of 5-chloro-2-[4-(4-carboxystyryl)phenyl]benzofuran in the procedure described in Example 27 above, there is obtained as the product 2-[4-(4-carbophenethyloxystyryl)phenyl]naphtho[1,2-b]furan.

EXAMPLE 39

Similarly, when phenethylamine is substituted for the dimethylamine hydrochloride and the potassium salt of 2[4-(3-carboxystyryl)phenyl]naphtho[1,2-b]furan for the potassium salt of 5-chloro-2-[4-(4-carboxystyryl)phenyl]benzofuran in the procedure described in Example 29 above, there is obtained as the product 2-[4(3-N-phenethylcarbamoylstyryl)phenyl]naphtho[1,2-b)furan.

EXAMPLE 40

Following the procedure described in Example 6 above but using sodium phenolate in place of methyl alcohol and 5-methoxy-2[4-(3-carboxystyryl) phenyl]benzofuran instead of 5-chloro-2-[4-(4-carboxystyryl)phenyl]benzofuran, there is obtained as the product 5-methoxy-2-[4-(3-carbophenoxystyryl)phenyl]benzofuran.

EXAMPLE 41

When n-hexyl bromide is substituted for the benzyl chloride and the sodium salt of 5-fluoro-2[4-(2-carboxystyryl)phenyl]benzofuran for the sodium salt of 5-chloro-2-[4-(4-carboxystyryl)phenyl]benzofuran in the procedure described in Example 27 above, there is obtained as the product 5-fluoro-2-[4-(2-carbo-n-hexyloxystyryl)phenyl]benzofuran.

EXAMPLE 42

Following the procedure described in Example 27 above but using t-butyl chloride in place of benzyl chloride and the sodium salt of 5-phenyl-2-[4-(4-carboxystyryl)phenyl]benzofuran for the sodium salt of 5-chloro-2-[4-(4-carboxystyryl)phenyl]benzofuran, there is obtained as the product 5-phenyl-2[4-(4-carbo-t-butyloxystyryl)phenyl)]benzofuran.

EXAMPLE 43

Similarly, when pyrrolidine is substituted for the dimethylamine hydrochloride in the procedure described in Example 29 above, there is obtained as the product 5-chloro-2-[4-(4-pyrrolidinocarbonylstyryl)phenyl]benzofuran.

EXAMPLE 44

When piperidine is substituted for the dimethylamine hydrochloride and the sodium salt of 5-methyl-2-[4-(2-carboxystyryl)phenyl]benzothiophene for the potassium salt of 5-chloro-2-[4-(4-carboxystyryl)phenyl]benzofuran in the procedure described in Example 29 above, there is obtained as the product 5-methyl-2-[4-(2-piperidinocarbonylstyryl)phenyl]benzothiophene.

EXAMPLE 45

Similarly, substituting morpholine for the dimethylamine hydrochloride and the potassium salt of 2-[4-(3-carboxystyryl)phenyl]naphtho[2,1-b]furan for the potassium salt of 5-chloro-2-[4-(4-carboxystyryl)phenyl]benzofuran in the procedure described in Example 29 above, the product 2-[4-(3-morpholinocarbonylstyryl)phenyl]naphtho[2,1-b]furan is obtained.

The dichlorobenzene and the trichlorobenzene used as recyrstallization solvents in the Examples above are industrial grade solvents which are mixtures of various isomers. Thus, the dichlorobenzene is predominately ortho dichlorobenzene containing some of the two isomers, meta and para; and the trichlorobenzene is predominantly 1,2,4-trichlorobenzene containing some of the other symmetrical and unsymmetrical trichlorobenzenes.

When the appropriate p-tolyl substituted compound of Formula III or Formula IV and the anil derivative of the appropriate aldehyde are interacted in a manner similar to that described in Example 1, there are obtained:

5-n-Propyl-7-ethyl-2-[3-methoxy-4-(3,4-dimethoxy-2-carboxy-styryl)phenyl]benzofuran from the interaction of 5-n-propyl-7-ethyl-2-(3-methoxy-4-tolyl)benzofuran and 6,7-dimethoxy-3-anilinophthalide;

4-Methoxy-7-bromo-2-[3-bromo-4-(3,5-dimethoxy-2-carboxystyryl)phenyl[benzothiophene from the interaction of 4-methoxy-7-bromo-2-(3-bromo-4-tolyl)benzothiophene and 5,7-dimethoxy-3-anilinophthalide;

5-Dimethylamino-2-[3-isopropyl-4-(2-bromo-4-carboxystyryl)phenyl]benzothiophene from the interaction of 5-dimethylamino-2-(3-isopropyl-4-tolyl)benzothiophene and the anil derivative of 3-bromoterephthalaldehydic acid;

5-Fluoro-7-iodo-2-[3-iodo-4-(6-propoxy-2-carboxystyryl)phenyl]benzofuran from the interaction of 5-fluoro-7-iodo-2-(3-iodo-4-tolyl)benzofuran and 4-propoxy-3-anilinophthalide;

7-n-Hexyl-2-[3-iodo-4-(4-fluoro-2-carboxystyryl)-phenyl]benzofuran from the interaction of 7-n-hexyl-2-(3-iodo-4-tolyl)benzofuran and 6-fluoro-3-anilinophthalide;

2-[3-Bromo-4-(4-bromo-2-carboxystyryl)phenyl]-naphtho[2,1-b]furan from the interaction of 2-(3-bromo-4-tolyl)naphtho-[2,1-b]furan and 6-bromo-3anilinophthalide;

5-(4-Ethylphenyl)-2-[3-chloro-4-(3-methoxy-2-carboxylstyryl)phenyl]benzothiophene from the interaction of 5-(4-ethylphenyl)-2-(3-chloro-4-tolyl)benzothiophene and 7-methoxy-3-anilinophthalide;

2-[3-n-Propyl-4-(2iodo-4-carboxystyryl)phenyl]naphtho[2,1-b]furan from the interaction of 2-(3-n-propyl-4-tolyl)naphtho-[2,1-b]furan and 3-iodoterephthalaldehydic acid;

5,7-Di-n-hexyl-2-[3-n-pentyl-4-(2-methyl-4-carboxystyryl)phenyl]benzothiophene from the interaction of 5,7-di-n-hexyl-2-(3-n-pentyl-4-tolyl)benzothiophene and the anil derivative of 3-methylterephthalaldehyde acid;

6-(4-Chlorophenyl)-2-[3-bromo-4-(3-methyl-2-carboxystyryl)phenyl]benzofuran from the interaction of 6-(4-chlorophenyl)-2-(3-bromo-4-tolyl)benzofuran and 7-methyl-3-anilinophthalide;

2-[3-n-Propyl-4-(4propoxy-6-methyl-3-carboxystyryl)-phenyl]naphtho[1,2-b]furan from the interaction of 2-(3-n-propyl-4-tolyl)naphtho[1,2-b]furan and the anil derivative of 4-methyl-6-propoxyisophthalaldehydic acid;

2-[3-Bromo-4-(3-n-butyl-2-carboxystyryl)phenyl]-naphtho[2,1-b]-furan from the interaction of 2-(3-bromo-4-tolyl)naphtho-[2,1-b]furan and 7-n-butyl-3-anilinophthalide;

5-Acetamido-2-[3-n-butyl-4-(5-chloro-2-carboxystyryl)phenyl]benzothiophene from the interaction of 5-acetamido-2-(3-n-butyl-4-tolyl)benzothiophene and 5-chloro-3-anilinophthalide;

5-Ethoxy-2-[3-n-pentyl-4-(4-iodo-2-carboxystyryl)-phenyl]benzothiophene from the interaction of 5-ethoxy-2-(3-n-pentyl-4-tolyl)benzothiophene and 6-iodo-3-anilinophthalide;

6-Methoxy-7-isopropoxy-2-[3-n-propyl-4-(3,5dimethoxy-2-carboxystyryl)phenyl]benzofuran from the interaction of 6-methoxy-7-isopropoxy-2-(3-n-propyl-4-tolyl)benzofuran and 5,7-dimethoxy-3-anilinophthalide;

2-[3-n-Propyl-4-(5-methoxy-2-carboxystyryl)phenyl]-naphtho-[2,1-b]furan from the interaction of 2-(3-n-propyl-4-tolyl)naphtho[2,1-b]furan and 5-methoxy-3-anilinophthalide;

2-[3-n-Propyl-4-(4-iodo-2-carboxystyryl)phenyl]naphtho[1,2-b]-furan from the interaction of 2-(3-n-propyl-4-tolyl)naphtho-[1,2-b]furan and 6-iodo-3-anilinophthalide;

5-(1-Methylpropyl)-2-[3-fluoro-4-(2-n-butyl-4-carboxystyryl)phenyl]benzofuran from the interaction of 5-(1-methylpropyl)-2-(3-fluoro-4-tolyl)benzofuran and the anil derivative of 3-n-butylterephthalaldehydic acid; and 2-[3-Iodo-4-(2bromo-4carboxystyryl)phenyl]naphtho[2,3-b]furan from the interaction of 2-(3-iodo-4-tolyl)naphtho-[2,3-b]furan and the anil derivative of 3-bromoterephthalaldehydic acid.

Esterification of the appropriate carboxylic acid-substituted compound of Formula I with the appropriate lower alkanol, lower alkanediol, phenol, benzyl alcohol or phenethyl alcohol according to the procedures described in Examples 6, 7 or 27 hereinabove, yields the following compounds:

5-Fluoro-7-iodo-2-[3-iodo-4-(6-propoxy-2-carboethoxystyryl)phenyl]benzofuran from the interaction of the acid chloride of 5-fluoro-7-iodo-2-[3-iodo-4-(6-propoxy-2-carboxystyryl)phenyl]benzofuran with ethyl alcohol;

5,7-Di-n-hexyl-2-[3-n-pentyl-4-(2-methyl-4-carbopropoxystyryl)phenyl]benzothiophene from the interaction of the acid chloride of 5,7-di-n-hexyl-2-[3-n-pentyl-4-(2-methyl-4-carboxystyryl)phenyl]benzothiophene with n-propyl alcohol;

2-[3-n-Propyl-4-(4-iodo-2carboisopropoxystyryl)-phenyl]naphtho[1,2-b]furan from the interaction of the acid chloride of 2-[3-n-propyl-4-(4-iodo-2-carboxystyryl)phenyl]naphtho[1,2-b]furan with isopropyl alcohol;

2-{3-n-Propyl-4-[2-iodo-4-carbo(3-hydroxypropoxy)-styryl]phenyl}naphtho[2,1-b]furan from the interaction of the acid chloride of 2-[3-n-propyl-4-(2-iodo-4-carboxystyryl)phenyl]naphtho[2,1-b]furan with 1,3-dihydroxypropane; 2-{3-Iodo-4-[2-bromo-4-carbo(2-hydroxypropoxy)styryl]phenyl}naphtho[2,3-b]furan from the interaction of the acid chloride of 2-[3-iodo-4-(2-bromo-4-carboxystyryl)phenyl]naphtho[23-b]-furan with 1,2-dihydroxypropane;

4Methoxy-7-bromo-2-[3-bromo-4-(3,5-dimethoxy-2-carbo-n-pentyloxystyryl)phenyl]benzothiophene from the interaction of the acid chloride of 4-methoxy-7bromo-2-[3-bromo-4-(3,5-dimethoxy-2-carboxystyryl)phenyl]benzothiophene with n-pentyl alcohol;

5-n-Propyl-7-ethyl-2-{3-methoxy-4-[3,4dimethoxy-2-carbo(2,6-dimethyl-4-bromophenoxy)styryl]phenyl-} benzofuran from the interaction of the acid chloride of 5-n-propyl-7-ethyl-2-[3-methoxy-4-(3,4-dimethoxy-2-carboxystyryl)phenyl]benzofuran with the sodium salt of 2,6-dimethyl-4-bromophenol;

2-{3-Bromo-4-[4-bromo-2-carbo(4-methyl-3-chlorobenzyloxy)styryl]phenyl}naphtho[2,1-b]furan from the interaction of the sodium salt of 2-[3-bromo-4-(4-bromo-2-carboxystyryl)phenyl]naphtho[2,1-b]furan with 4-methyl-3-chlorobenzyl chloride;

5-Fluoro-7-iodo-2-{3-iodo-4-[6-propoxy-2-carbo(3-methylphenethyloxy)styryl]phenyl}benzofuran from the interaction of the sodium salt of 5-fluoro-7-iodo-2-[3-iodo-4-(6-propoxy-2-carboxystyryl)phenyl]-benzofuran with 3-methylphenethyl bromide;

7-n-Hexyl-2-{3-iodo-4-[4-fluoro-2-carbo(3-bromobenzyloxy)styryl]phenyl}benzofuran from the interaction of the sodium salt of 7-n-hexyl-2-[3-iodo-4-(4-fluoro-2-carboxystyryl)phenyl]benzofuran and 3-bromobenzyl bromide; and 5-Dimethylamino-2-{3-isopropyl-4-[2-bromo-4-carbo(2-methoxyphenethyloxy)styryl]phenyl}benzothiophene from the interaction of 5-dimethylamino-2-[3-isopropyl-4-(2-bromo-4-carboxystyryl)phenyl]-benzothiophene with 2-methoxyphenethyl bromide.

Amidation of the appropriate carboxylic acid-substituted compound of Formula I with the appropriate amines according to the procedure described in Example 29 hereinabove, yields the following compounds:

5-(4-Ethylphenyl)-2-[3-chloro-4-(3-methoxy-2-N-propyl-N-phenyl-carbamoylstyryl)phenyl]benzothiophene from the interaction of the acid chloride of 5(4-ethylphenyl)-2-[3-chloro-4-(3-methoxy-2-carboxystyryl)phenyl]benzothiophene with N-n-propylaniline;

6-(4-Chlorophenyl)-2-[3-bromo-4-(3-methyl-2-N-methyl-N-phenethylcarbamoylstyryl)phenyl]benzofuran by reacting the acid chloride of 6-(4-chlorophenyl)-2-[3-bromo-4-(3-methyl-2-carboxylstyryl)-phenyl]benzofuran with N-methylphenethylamine;

2-[3-Bromo-4-(3-n-butyl-2-p-methoxybenzylcarbamoylstyryl)phenyl]-naphtho[2,1-b]furan by condensing the acid chloride of 2-[3-bromo-4-(3-n-butyl-2-carboxystyryl)phenyl]naphtho[2,1-b]furan with p-methoxybenzylamine;

2-[3-Bromo-4-(3-n-butyl-2p-pentoxyphenylcarbamoylstyryl)phenyl]-naphtho[2,1-b]furan from the interaction of the acid chloride of 2-[3-bromo-4-(3-n-butyl-2-carboxystyryl)phenyl]naphtho[2,1-b]furan with p-pentoxyphenylamine;

6-Methoxy-7-isopropoxy-2-[3-n-propyl-4-(3,5-dimethoxy-2-N-methyl-N-3-methylphenylcarbamoylstyryl)-phenyl]benzofuran from the interaction of the acid chloride of 6-methoxy-7-isopropoxy-2-[3-n-propyl-4-(3,5-dimethoxy-2-carboxystyryl)phenyl]benzofuran and N-methyl-m-toluidine;

2-[3-Iodo-4-(2-bromo-4-N-methyl-N-p-methoxybenzylcarbamoylstyryl)phenyl]naphtho[2,3-b]furan by condensing the acid chloride of 2-[3-iodo-4-(2-bromo-4-carboxystyryl)phenyl]naphtho[2,3-b]furan with N-methylmethoxybenzylamine;

5-(4-Ethylphenyl)-2-[3-chloro-4-(3-methoxy-2-pyrrolidinocarbonylstyryl)phenyl]benzothiophene by reacting the acid chloride of 5-(4-ethylphenyl)-2-[3-chloro-4-(3-methoxy-2-carboxystyryl)phenyl]benzothiophene with pyrrolidine;

2-[3-n-Propyl-4-(4-iodo-2-morpholinocarbonylstyryl)-phenyl]naphtho[1,2-b]furan from the interaction of the acid chloride of 2-[3-n-propyl-4-(4-iodo-2-carboxystyryl)phenyl]naphtho[1,2-b]furan with morpholine;

5-(1-Methylpropyl)-2-[3-fluoro-4(2-n-butyl-4-piperidinocarbonylstyryl)phenyl]benzofuran by condensing the acid chloride of 5-(1-methylpropyl)-2-[3-fluoro-4-(2-n-butyl-4-carboxystyryl)phenyl]benzofuran with piperidine;

5-Ethoxy-2-[3-n-pentyl-4-(4-iodo-2-morpholinocarbonylstyryl)phenyl]benzothiophene from the interaction of the acid chloride of 5-ethoxy-2-[3-n-pentyl-4-(4-iodo-2-carboxystyryl)phenyl]benzothiophene with morpholine;

2-[3-n-Propyl-4-(5-methoxy-2-pyrrolidinocarbonylstyryl)phenyl]naphtho[2,1-b]furan by reacting the acid chloride of 2-[3-n-propyl-4-(5-methoxy-2-carboxystyryl)phenyl]naphtho[2,1-b]furan with pyrrolidine;

5-Fluoro-7-iodo-2-[3-iodo-4-(6-propoxy-2-piperidinocarbonylstyryl)phenyl]benzofuran by reacting the acid chloride of 5-fluoro-7-iodo-2-[3-iodo-4-(6-propoxy-2-carboxystyryl)phenyl]benzofuran with piperidine;

5,7-Di-n-hexyl-2-{3-n-pentyl-4-[2-methyl-4-(2-bromo-3,4-dimethoxy)phenethylcarbamoylstyryl]phenyl-}benzothiophene from the interaction of acid chloride of 5,7-di-n-hexyl-2-[3-n-pentyl-4-(2-methyl-4-carboxystyryl)phenyl]benzothiophene and 2-bromo-3,4-dimethoxyphenethylamine; and 5-Fluoro-7-iodo-2-{3-iodo-4-[6-propoxy-2-(4-methoxy)-N-methylphenethylcarbamoylstyryl]phenyl}benzofuran by reacting the acid chloride of 5-fluoro-7-iodo-2-[3-iodo-4-(6-propoxy-2-carboxystyryl)-phenyl]benzofuran with 4-methoxy-N-methylphenethylamine.

The effectiveness of the optical brightening agents prepared above is determined by a variety of tests. The tests include dyeings made on various fabrics. Such dyeings can be accomplished by subjecting cloth samples to repeated launderings from detergent solutions containing optical brightening quantities of the compounds. Another method previously described hereinabove is to impregnate textile fibers from an aqueous dispersion followed by heat treating of the impregnated fibers. Still another method involves the incorporation of the compound to be tested into a polymeric melt. In each of these tests, the substrate treated with the optical brightening agent is subjected to color comparison with untreated samples of the same substrate. A color difference meter is used to measure differences in shade of whiteness between the samples. The following procedure, which is illustrative of one of these methods for determining the effectiveness of the optical brightening agents of this invention, describes the test method and the results obtained for the compound of Example 5, a particularly preferred compound for incorporation into normally solid, fiber and film-forming polymeric materials, when incorporated into polyethylene terephthalate melts.

A solution of 5-chloro-2-[4-(4-carboxystyryl)-phenyl]benzofuran (Example 5) in dimethyl terephthalate was prepared by intermixing 0.04 g of the brightener with 10.00 g of dimethyl terephthalate and then melting the two solids together, with continual stirring and under a carbon dioxide atmosphere, by imersing the container in a bath of diethyl phthalate which was then heated to 200°C during a period of about 15–20 minutes. The fluid mixture was then poured into a mortar and ground to a fine powder. The solid solution of brightener in dimethyl terephthalate was incorporated into polyethylene terephthalate by blending 1.5 g of the brightener-dimethyl terephthalate powder with 18.0 g of predried polyethylene terephthalate chips and 0.5 g of dimethyl terephthalate. The mixture was melted under a carbon dioxide atmosphere by immersing the container in a bath of diethyl phthalate at 115°C after which the bath was heated to boiling (295°–7°C). The melt was stirred for 5 minutes, and it then was removed from the bath and allowed to cool to room temperature, continually under carbon dioxide. The polyethylene terephthalate casting was then broken up and ball milled with stoneware pellets in distilled water. The particles were dried and screened, and those passing through a 40 mesh screen were packed into a 5 cm polystyrene Petri dish. The color of the sample was then measured on a color difference meter (Hunterlab Model D-25, Hunter Associates laboratory, McLean, Va.) in comparison with a standard magnesium oxide plate. These values were then compared with those for a blank sample prepared in the identical way except that the optical brightener was omitted. The values of the blank sample were determined at the same time as those of the sample tested. Following are the readings obtained in comparison with the standard magnesium oxide plate:

| Hunterlab D-25 Readings | | | |
|---|---|---|---|
| | L | a | b |
| Blank polyethylene terephthalate (PET) | 96.2 | +0.5 | +2.6 |
| PET containing 0.03 percent 5-chloro-2-[4-(4-carboxystyryl)-phenyl]benzofuran | 96.6 | +3.2 | −3.4 |

These results show that the shade of whiteness imparted to the polyethylene terephthalate was in the pink and blue range considered most desirable in the textile art. For the significance of the values recorded above, see R. S. Hunter, Photoelectric Color Difference Meter, J. Opt. Soc. Am., 48, 985 (1958).

We claim:
1. A compound having low water solubility of the formula

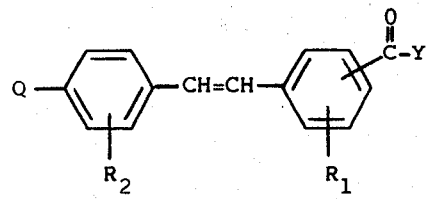

wherein:
Q is a monovalent aromatic heterocyclic radical selected from the class having the formulas

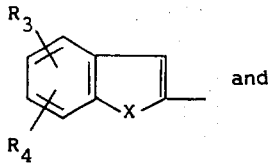  and

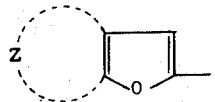

X is oxygen or sulfur;
Y is —OR or

in which
R is hydrogen, lower akyl having one to six carbon atoms, hydroxy-lower alkyl having two or three carbon atoms, phenyl, benzyl, phenethyl or phenyl, benzyl or phenethyl substituted in the benzene ring thereof by lower alkyl of one to six carbon atoms, halo or alkoxy of one to six carbon atoms;
R° is hydrogen, lower alkyl having one to three carbon atoms, phenyl, benzyl, phenethyl or phenyl, benzyl or phenethyl substituted in the benzene ring thereof by lower alkyl of one to six carbon atoms, halo or alkoxy of one to six carbon atoms;
Y° is hydrogen or lower having one to three carbon atoms;
R° and Y° taken together with the nitrogen atom to which they are commonly bonded are pyrrolidino, piperidino or morpholino;
$R_1$ and $R_2$ are the same or different and are members of the class consisting of hydrogen, alkyl having one to six carbon atoms, alkoxy having one to six carbon atoms, and halo;
$R_3$ and $R_4$ are the same or different and are members of the class consisting of hydrogen, alkyl having one to six carbon atoms, alkoxy having one to six carbon atoms, cyano, halo, dialkylamino wherein each alkyl has one to six carbon atoms, alkanoylamino having one to six carbon atoms, phenyl, phenyl substituted by alkyl having one to six carbon atoms, halo, alkoxy having one to six carbon atoms, and alkanoylamino having one to six carbon atoms; and
Z is naphtho.
2. A compound according to claim 1 of the formula

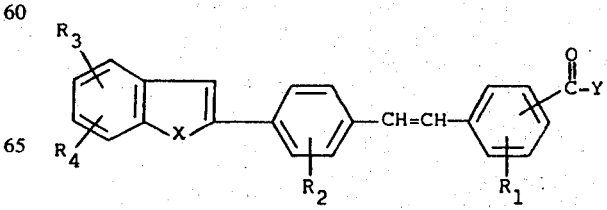

3. A compound according to claim 2 of the formula

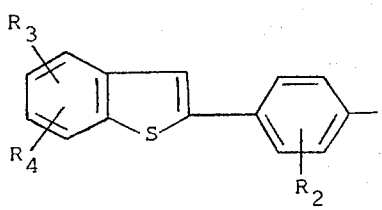

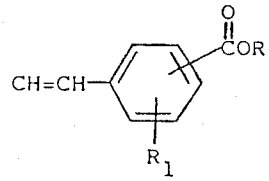

4. 2-[4-(4-Carboxystyryl)phenyl]benzothiophene according to claim 3.

5. A compound according to claim 2 of the formula

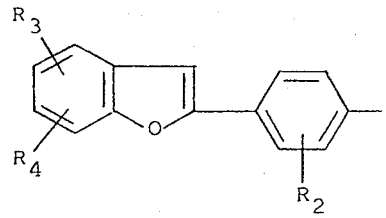

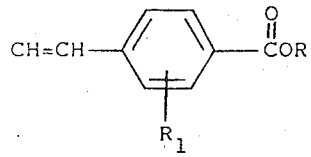

6. 2-[4-(4-Carboxystyryl)phenyl]benzofuran according to claim 5.
7. 5-Phenyl-2-[4-(4-carboxystyryl)phenyl]benzofuran according to claim 5.
8. 5-Methoxy-2-[4-(4-carboxystyryl)phenyl]benzofuran according to claim 5.
9. 5-Chloro-2-[4-(4-carboxystyryl)phenyl]benzofuran according to claim 5.
10. 5-Chloro-2-[4-(4-carbomethoxystyryl)phenyl]benzofuran according to claim 5.
11. 5-Chloro-2-{4-[4-carbo(2-hydroxyethoxy)styryl]phenyl}benzofuran according to claim 5.
12. 5-Chloro-2-[4-(2-carboxystyryl)phenyl]benzofuran according to claim 5.
13. 5,6-Dichloro-2-[4-(4-carboxystyryl)phenyl]benzofuran according to claim 5.
14. 5-Fluoro-2-[4-(4-carboxystyryl)phenyl]benzofuran according to claim 5.
15. 5-Methyl-2-[(4(4-carboxystyryl)phenyl]benzofuran according to claim 5.
16. 5-Cyano-2-[(4-(4-carboxystyryl)phenyl]benzofuran according to claim 5.
17. 5-Chloro-2-[4-(3-carboxystyryl)phenyl]benzofuran according to claim 5.
18. 5-Chloro-2-[4-(4-carbobenzyloxystyryl)phenyl]benzofuran according to claim 5.
19. A compound according to claim 2 of the formula

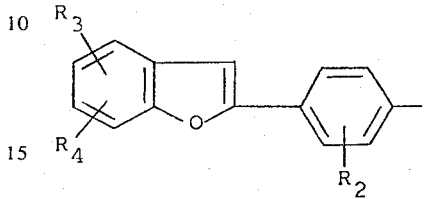

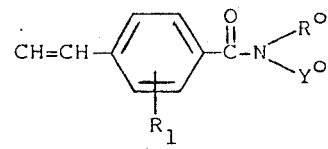

20. 5-Chloro-2-[4-(4N,N-dimethylcarbamoylstyryl)phenyl]-benzofuran according to claim 19.
21. A compound according to claim 1 of the formula

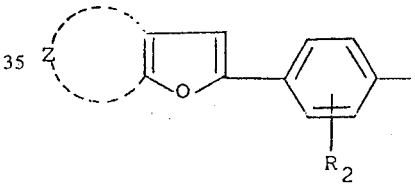

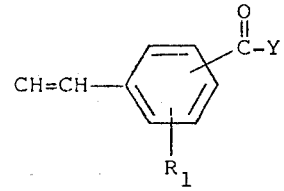

22. A compound according to claim 21 of the forula

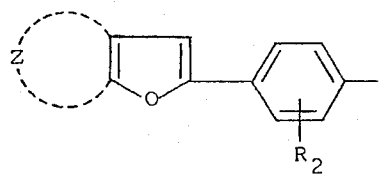

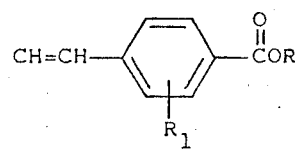

23. A compound according to claim 1 of the formula
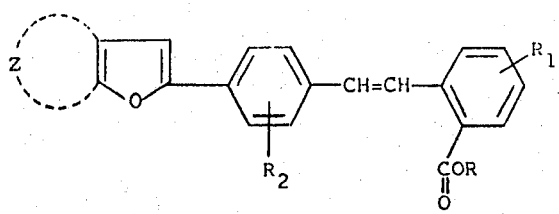
24. 2-[4-(2-Carboxystyryl)phenyl]naphtho[1,2-b]furan according to claim 23.
25. 2-[4-(2-Carboxystyryl)phenyl]naphtho[2,1-b]furan according to claim 23.
* * * * *

UNITED STATES PATENT AND TRADEMARK OFFICE
CERTIFICATE OF CORRECTION

PATENT NO. : 3,974,144
DATED : August 10, 1976
INVENTOR(S) : Nathan N. Crounse and Kantilal B. Desai It is certified that error appears in the above-identified patent and that said Letters Patent are hereby corrected as shown below:

Column 1, line 4, "contiuation" should read -- continuation --.

Column 2, line 12, "cosisting" should read -- consisting --.

Column 2, line 65, "compund" should read -- compound --.

Column 3, line 28, "compund" should read -- compound --.

Column 4, line 51, "$-CH_2CH_2Ch_2OH$" should read -- $-CH_2CH_2CH_2OH$ --.

Column 5, line 22, "valeramide" should read -- valeramido --.

Column 5, line 43, "blue-water" should read -- blue-white --.

Column 5, line 50, "fibrics" should read -- fabrics --.

Column 6, line 13, "isophthalaldehyde" should read -- isophthalaldehydic --.

Column 6, line 51, "reagert" should read -- reagent --.

Column 22, line 24, "akyl" should read -- alkyl --.

Column 22, Claim 1, line 37, "lower having" should read -- lower alkyl having --.

UNITED STATES PATENT AND TRADEMARK OFFICE
CERTIFICATE OF CORRECTION

PATENT NO. : 3,974,144
DATED : August 10, 1976
INVENTOR(S) : Nathan N. Crounse and Kantilal B. Desai It is certified that error appears in the above-identified patent and that said Letters Patent are hereby corrected as shown below:

Column 23, Claim 15, line 67, "[(4(4-carboxystyryl)" should read -- [4-(4-carboxystyryl) --.

Column 24, Claim 16, line 2, "[(4-(4-carboxystyryl)" should read -- [4-(4-carboxystyryl) --.

Column 24, Claim 20, lines 28 and 29, "(4N,N-dimethylcarbamoylstyryl)phenyl]-benzofuran" should read -- (4-N,N-dimethylcarbamoylstyryl)phenyl]benzofuran --.

Column 24, Claim 22, line 51, "forula" should read -- formula --.

Column 25, Claim 23, line 1, "1" should read -- 21 --.

Signed and Sealed this

Twentieth Day of June 1978

[SEAL]

Attest:

RUTH C. MASON
Attesting Officer

DONALD W. BANNER
Commissioner of Patents and Trademarks